United States Patent [19]

Lim

[11] 4,409,331

[45] * Oct. 11, 1983

[54] PREPARATION OF SUBSTANCES WITH ENCAPSULATED CELLS

[75] Inventor: Franklin Lim, Richmond, Va.

[73] Assignee: Damon Corporation, Needham Heights, Mass.

[*] Notice: The portion of the term of this patent subsequent to Oct. 5, 1999 has been disclaimed.

[21] Appl. No.: 372,835

[22] Filed: Apr. 28, 1982

Related U.S. Application Data

[63] Continuation-in-part of Ser. No. 243,583, Mar. 13, 1981, abandoned, which is a continuation-in-part of Ser. No. 24,600, Mar. 28, 1979, Pat. No. 4,352,883, which is a continuation-in-part of Ser. No. 953,413, Oct. 23, 1978, abandoned.

[51] Int. Cl.$^3$ .................. C12N 11/10; C12N 11/04; C12N 5/00; C12N 5/02
[52] U.S. Cl. .................................. 435/178; 435/182; 435/240; 435/241; 424/93; 424/DIG. 7
[58] Field of Search .............. 435/174, 177, 178, 180, 435/182, 240, 241; 424/DIG. 7, 93

[56] References Cited

U.S. PATENT DOCUMENTS

| | | | |
|---|---|---|---|
| 3,522,346 | 7/1970 | Chang | 435/188 X |
| 3,725,113 | 4/1973 | Chang | 424/101 X |
| 3,730,841 | 5/1973 | Salvatore et al. | 435/182 |
| 3,733,205 | 5/1973 | Shovers et al. | 435/262 X |
| 3,827,565 | 8/1974 | Matsumura | 435/182 X |
| 3,860,490 | 1/1975 | Guttag | 435/182 |
| 4,138,292 | 2/1979 | Chibata et al. | 435/178 |
| 4,251,387 | 2/1981 | Cim et al. | 424/DIG. 7 |

FOREIGN PATENT DOCUMENTS

| | | |
|---|---|---|
| 2835875 | 4/1980 | Fed. Rep. of Germany . |
| 1600988 | 9/1970 | France . |
| 1422854 | 1/1976 | United Kingdom . |
| 1506112 | 4/1978 | United Kingdom . |
| 1520217 | 8/1978 | United Kingdom . |
| 1525665 | 9/1978 | United Kingdom . |
| 1545545 | 5/1979 | United Kingdom . |
| 1553190 | 9/1979 | United Kingdom . |
| 1556584 | 11/1979 | United Kingdom . |
| 2046271 | 11/1980 | United Kingdom . |

OTHER PUBLICATIONS

Kierstan et al., The Immobilization of Microbial Cells, Subcellular Organelles and Enzymes in Calcium Alginate Gels, Biotech. and Bioeng., vol. XIX, 1977, (pp. 387–397).

Tze et al., Implantable Artificial Endocrine Pancreas Unit Used to Restore Normoglycemia in Diabetic Rat, Nature, vol. 264, 1976, (pp. 466–467).

Chang, T. M. S., Biomedical Applications of Immobilized Enzymes and Proteins, vol. I, Plenum Press, N.Y., 1977, pp. 69–90 and 147–153.

Primary Examiner—David M. Naff
Attorney, Agent, or Firm—Lahive & Cockfield

[57] ABSTRACT

Disclosed is a system and process for producing substances produced in cells such as antibodies and biological response modifiers. Cells which produce the substance of interest are encapsulated within semipermeable membranes having an upper limit of permeability sufficient to allow traverse of ions, amino acids and other cell nutrients and then suspended in a culture medium. Serum components or other high molecular weight materials needed for ongoing viability and normal in vitro metabolism of certain types of cells may be included within the intracapsular volume and may be excluded from the extracapsular medium by limiting the permeability of the membranes. The substance of interest collects either in the intracapsular volume or the extracapsular medium, depending on the degree of permeability of the membranes and on the molecular weight of the substance.

25 Claims, 2 Drawing Figures

PREPARATION OF SUBSTANCES WITH ENCAPSULATED CELLS

REFERENCE TO RELATED APPLICATIONS

This application is a continuation-in-part of copending U.S. application Ser. No. 243,583, filed Mar. 13, 1981, now abandoned, which was a continuation in part of U.S. application Ser. No. 24,600, filed Mar. 28, 1979, now U.S. Pat. No. 4,352,883 which is a continuation-in-part of U.S. application Ser. No. 953,413, filed Oct. 23, 1978 (now abandoned). Related U.S. applications include copending Ser. Nos. 243,584, now abandoned, and 243,586 which were filed on Mar. 13, 1981.

BACKGROUND OF THE INVENTION

This invention relates to a method of producing biological materials of the type generated by cells.

Advances in cellular biology have shown that the cells of various higher organisms produce small quantities of substances having significant potential or demonstrable utility for the treatment or diagnosis of disease. Examples of such substances abound in the literature and include various biological response modifiers such as hormones, interferons, and lymphokines, as well as other substances such as antibodies used in diagnostic testing. Cell cultures of microbial origin have long been used to produce large quantities of antibiotics.

Especially in cell cultures derived from higher animals, there is an ever present danger of bacterial or other contamination. Also, in most instances the quantities of the substance of interest produced by cell cultures are very small and collect in the culture medium which contains a complex mixture of serum proteins and other substances. This make isolation and purification of the substance of interest difficult.

SUMMARY OF THE INVENTION

This invention provides a system and process for producing substances which are produced by living cells. The practice of the invention has the inherent dual advantages of providing a protective environment for the cells of the culture and providing a means of collecting substances of interest in a medium having fewer admixed extraneous components. The invention may be used to separate the substance of interest from higher molecular weight serum proteins and the like normally required to support the ongoing viability and metabolism of the producing cells. Alternatively, the invention may be used to collect the substance of interest in a medium containing relatively small quantities of low molecular weight nutrients or cell metabolic products.

The process comprises the steps of encapsulating cells within a membrane which is permeable to the nutrients, ions, and other relatively low molecular weight materials needed for normal metabolism and ongoing viability of the cells. The membrane may or may not be permeable to the substance of interest secreted by the cells, but in any case will have an upper limit of permeability sufficient to allow traverse of molecules having a molecular weight of some selected level generally below about $2.0 \times 10^5$ daltons. The capsules so produced are suspended in a conventional aqueous culture medium, and the encapsulated cells are allowed to undergo normal in vitro metabolism. Substances of a molecular weight below the upper permeability limit of the membrane which are secreted by the cells permeate the membrane and collect in the culture medium. Advantageously, high molecular weight substances such as serum proteins which are required for health and viability of many types of cell cultures from higher animals, but which typically are themselves not consumed, may be included in the microcapsules where they are confined and prevented from diffusing into the culture medium. Substances which the cell culture consumes during metabolism having a molecular weight low enough to permit diffusion through the capsule membranes pass therethrough from the culture medium. Metabolic products of the cells having molecular dimension sufficiently small to allow passage through the membrane diffuse into the medium external to the capsules. The substances of interest, if of a molecular weight below the upper limit of permeability, diffuse into the extracapsular medium where they can be harvested relatively easily because of the absence of contaminating higher molecular weight materials present in prior art unencapsulated cell cultures. If the substance of interest has a molecular weight in excess of the upper limit of permeability of the membranes, then it collects in the capsules which may subsequently be isolated from the medium and disrupted for recovery procedures.

The invention is essentially unlimited with respect to the types of cells which may be included within the capsule membranes. Specifically, it is contemplated that cultures of cells from the tissue of all higher animals as well as microorganisms may be employed. Fused cells, e.g., hybridoma cells, or genetically modified cells produced, for example, by the emerging recombinant DNA technology, can likewise be encapsulated without difficulty. In short, provided there exists a culture medium operable to maintain in vitro the cell type in question, that cell type can be utilized in accordance with the techniques disclosed herein. Non-limiting examples of the types of substances that may be produced in accordance with the process and by the system of the invention include insulin, glycogen, prolactin, somatostatin, thyroxin, steroid hormones, pituitary hormones, interferons, folliclestimulating hormones (FSH), PTH, and antibodies.

The system of the invention comprises encapsulated viable cells suspended in an aqueous culture medium. The encapsulated cells comprise membranes characterized by an upper limit of permeability sufficient to allow traverse of the nutrients needed for cell metabolism and ongoing viability. The membranes enclose viable cells disposed in a medium which includes all components needed to maintain metabolism of the cells and which are of a size range in excess of the upper permeability limit of the membrane. The culture medium comprises components needed to maintain viability of the cells which have a molecular weight below the upper permeability limit of the membranes.

Accordingly, an object of the invention is the provision of a system and method for producing biological materials of the type produced by cells. Another object of the invention is to provide such a system wherein the producing cells are contained within a protective, healthful microenvironment confined by a semipermeable membrane which serves to separate products of cell metabolism from high molecular weight materials needed for viability and maintenance of the cells. Another object is to provide an improved process for producing biologically active materials from cell cultures. Yet another object is to produce antibodies and biologial response modifiers such as hormones, interferons, and lymphokines in a serum-free medium.

These and other objects and features of the invention will be apparent from the following description and from the drawing wherein.

DESCRIPTION

The broad concept of the invention is to interpose a semipermeable membrane about individual cells or groups of cells so as to provide a microenvironment for the cells complete with the cell culture medium and separated by the membrane from an external aqueous medium. Cells of mammalian origin typically require for ongoing health and viability the presence of serum proteins, a portion of which have a molecular weight in excess of about 65,000–150,000 daltons. In the prior art technique of unencapsulated cell culturing, materials of interest secreted from the cells are dispersed in the culture medium and mixed with both high and low molecular weight components. Since the quantities of cell-produced products are typically rather small, isolation of the substance of interest becomes an arduous purification task. Furthermore, mammalian cell cultures are notoriously sensitive to contamination by bacterial or other sources. This necessitates that culturing be conducted using various techniques to maintain sterility and often that antibiotics be included in the medium.

According to the practice of this invention, the foregoing difficulties are alleviated by encapsulating the cells of the culture within semipermeable membranes having a selected limit of permeability generally no greater than about 200,000 daltons, that is, the membrane contains pores which allow substances having a maximum molecular weight at or below the upper permeability limit to traverse the membrane whereas substances of molecular weight above the upper permeability limit are precluded from traversing the membrane. This allows one to encapsulate cells together with a culture medium containing all components needed for ongoing viability, metabolism, and even mitosis, and then to suspend the so encapsulated cells in a culture medium which contains lower molecular weight substances consumed by the cells but which need not include the required high molecular weight substances.

Typically, cells from higher organisms do not ingest high molecular weight serum proteins and the like, but rather require them in close proximity for ongoing normal biological responses. Salts, amino acids and other lower molecular weight factors which are ingested or metabolized by the cells pass freely through the membrane and may be replenished as needed by simple change of the culture medium external to the capsules. Secreted products of cell metabolism having a molecular weight below the upper limit of membrane permeability collect in the extracapsular medium, where, because of the absence in the medium of the high molecular weight materials, harvesting and isolation of the metabolic products of interest are simplified. Harvesting of products of interest having a molecular weight above the upper permeability limit is also aided in that such products collect within the capsules and are not dispersed in the extracapsular volume.

Figure 1:
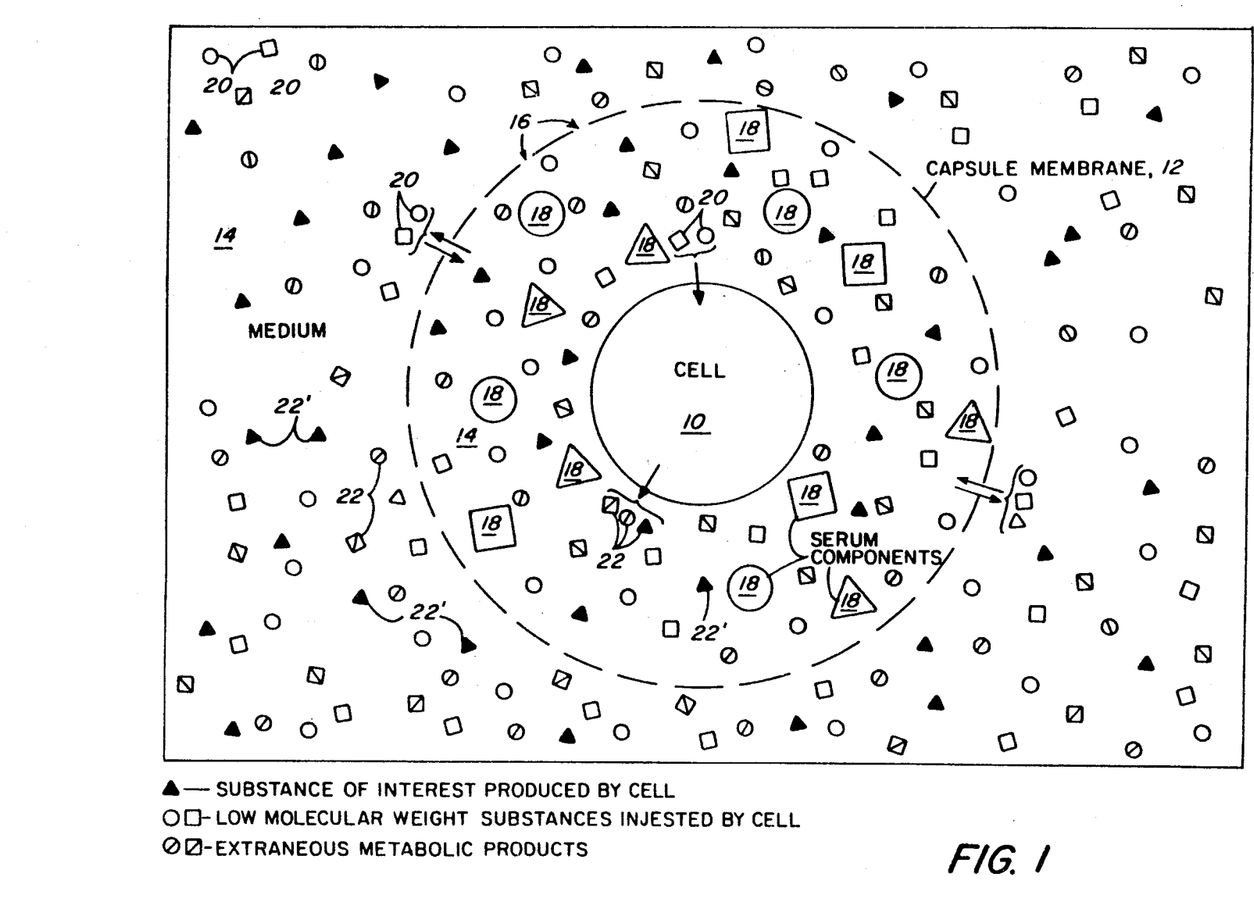
FIG. 1 is a schematic diagram illustrating the concept of the invention and FIG. 2 is a graph showing the results of the experiment described in example 5.

The concept of the invention, as applied to lower molecular weight cell products, is schematically illustrated in the drawing. As shown, a cell 10 is disposed within a capsule membrane 12 having pores 16. High molecular weight factors 18 are enclosed within membrane 12 and are free to circulate within the confines of the membrane in the medium 14. Components 20 needed by the cell as well as metabolic products 22 including the substance of interest 22' freely circulate in both the intracapsular and extracapsular medium and traverse the membrane through pores 16. As required on a periodic (or continuous) basis, the extracapsular medium together with all of its components can be separated by aspiration or the like from the capsules themselves and replaced with fresh medium. The collected medium will be substantially free of high molecular weight components 18, thus simplifying the harvesting and isolation procedures. Furthermore, the cell 10 remains protected within the intracapsular microenvironment at all times.

In some cases, e.g., in order to stimulate production by encapsulated cells of a particular substance of interest, it is required to subject the cells to high molecular weight components having molecular dimensions too large to traverse the membrane. An example is the production of interferon from human fibroblasts, leukocytes, or lymphoblastoid cells which are induced to secrete interferon by treatment with certain viruses or high molecular weight nucleic acids. In such a case, if the upper permeability limit of the membranes is less than the molecular weight of the inducing factor, the cells must be subjected to interferon induction prior to encapsulation, or the capsule membranes, after culture of the cells, must be selectively disrupted to allow such high molecular weight materials to be ingested by the cell. Copending application Ser. No. 243,584, discloses a method of selectively disrupting certain types of capsule membranes which may be used for these and other purposes without damage to the cells.

The process of the invention depends on one's ability to form semipermeable membranes about cells without simultaneously adversely affecting their ongoing viability. One suitable encapsulation process is set forth in detail below.

Cell Encapsulation

The tissue or cells to be encapsulated are suspended in an aqueous medium suitable for maintenance or for supporting the ongoing metabolic processes of the particular tissue or cell type involved. Media suitable for this purpose are available commercially. The average diameter of the material to be encapsulated can vary widely between a few micrometers to several millimeters. However, best results are achieved with capsules of a size in the range of 300–1000 micrometers. Mammalian islets of Langerhans are typically 50 to 200 micrometers in diameter. Individual cells such as fibroblasts, leukocytes, lymphoblastoids, pancreatic beta cells, alpha cells, delta cells, various ratios thereof, or other tissue units may be encapsulated as desired. Also, microorganisms may be encapsulated including those which have been genetically modified by recombinant DNA or other techniques.

The ongoing viability of such living matter is dependent, inter alia, on the availability of required nutrients, oxygen transfer, absence of toxic substances in the medium, and the pH of the medium. Heretofore, it has not been possible to maintain such living matter in a physiologically compatible environment while simultaneously encapsulating. The problem has been that the conditions required for membrane formation have been lethal or harmful to the tissue, and prior to the invention of U.S. Pat. No. 4,352,883, no method of membrane formation which allowed tissue to survive in a healthy state had been forthcoming.

However, it has been discovered that certain water-soluble substances which are physiologically compatible with living tissue and can be rendered water-insoluble to form a shape-retaining, coherent mass, can be used to form a "temporary capsule" or protective barrier layer about individual cells or groups of cells and that this temporary capsule can be treated to deposit a more permanent semipermeable membrane about the cells without damage to the cells. Such a substance is added, typically at a concentration on the order of a few weight percent, to the tissue culture medium, which also contains cells of the culture, serum components (if required) and optionally, a cellular substrate such as collagen or another high molecular weight, water dispersible material which acts as an anchoring substrate. When using collagen, the concentration should be within the range of about 10 ug/ml to about 1 mg/ml, but preferably on the order of 100–500 ug/ml.

The solution is then formed into droplets containing tissue together with its medium and is immediately rendered water-insoluble and gelled, at least in a surface layer. Thereafter, the shape-retaining temporary capsules are provided with a more permanent membrane which may itself subsequently be selectively disrupted if it is desired to release the tissue without damage. Where the material used to form the temporary capsules permits, the capsule interior may be reliquified after formation of the permanent membrane. This is done by reestablishing the conditions in the medium at which the material is soluble.

The material used to form the temporary capsules may be any non-toxic, water-soluble material which, by a change in ionic environment or concentration, can be converted to a shape-retaining mass. The material should also contains plural, easily ionized anionic moieties, e.g., carboxyl groups, which can react by salt formation with polymers containing plural cationic groups. As will be explained below, use of this type of material enables one to deposit a permanent membrane of a selected upper limit of permeability without difficulty in surface layers of the temporary capsule.

The presently preferred materials for forming the temporary capsule are acidic, water-soluble, natural or synthetic polysaccharide gums. Such materials are commercially available. They are typically extracted from vegetable matter and are often used as additives to various foods. Sodium alginate is the presently preferred water-soluble gum. Alginate in the molecular weight range of 150,000+ daltons may be used, but because of its molecular dimensions and viscosity will usually be unable to permeate the finally formed capsule membranes. Lower molecular weight alginate, e.g., 50,000–80,000 daltons, is more easily removed from the intracapsular volume by diffusion through a membrane of sufficient porosity and is therefore preferred. Other useable gums include acidic fractions of guar gum, carageenan, pectin, tragacanth gum, or xanthan gum.

These materials comprise glycoside-linked saccharide chains. Their free acid groups are often present in the alkali metal ion form, e.g., sodium form. If a multivalent ion such as calcium or aluminum is exchanged for the alkali metal ion, the water-soluble polysaccharide molecules are "cross-linked" to form a water-insoluble, shape-retaining gel which can be resolublized on removal of the ions by ion exchange or via a sequestering agent. While essentially any multivalent ion which can form a salt with the acidic gum is operable, it is preferred that physiologically compatible ions, e.g., calcium, be employed. This tends to preserve the tissue in the living state. Other multivalent cations can be used. Magnesium ions are ineffective in gelling sodium alginate.

A typical solution composition comprises equal volumes of a cell culture in its medium and a one or two percent solution of gum in physiological saline. When employing sodium alginate, a 0.6 to 1.2 percent solution has been used with success. If the cells to be encapsulated are of the type which require attachment to an anchoring substrate to undergo mitosis, and if the cells are to be grown within the capsules, then collagen or another high molecular weight or other microparticle water-dispersible protein or polypeptide, either natural or synthetic, may be included in the cell culture, and will be confined within the intracapsular volume of the finally formed capsules. If a polymer having plural cationic groups, e.g., polylysine, is employed for this purpose, the cationic groups react with anionic sites on the water-soluble gum to form a substantially water-insoluble matrix intertwined with the gum. Preferred concentrations for such materials are on the order of 100–500 ug/ml of suspension (including gum solution).

In the next step of the encapsulation process, the gum solution containing the tissue is formed into droplets of a desired size. Thereafter, the droplets are immediately gelled to form shape-retaining spherical masses preferably but not necessarily in spherical or spheroidal form. The drop formations may be conducted by known methods. An exemplary procedure follows.

A tube containing an aqueous solution of multivalent cations, e.g., 1.5% $CaCl_2$ solution, is fitted with a stopper which holds a drop forming apparatus. The apparatus consists of a housing having an upper air intake nozzle and an elongate hollow body friction fitted into the stopper. A 10 cc syringe equipped with a stepping pump is mounted atop the housing with, e.g., a 0.01 inch I.D. Teflon coated needle passing through the length of the housing. The interior of the housing is designed such that the tip of the needle is subjected to a constant laminar air flow which acts as an air knife. In use, with the syringe full of solution containing the material to be encapsulated, the stepping pump is actuated to incrementally force droplets of solution from the tip of the needle. Each drop is "cut off" by the air stream and falls approximately 2.5 cm into the $CaCl_2$ solution where it is immediately gelled by absorption of calcium ions. The distance between the tip of the needle and the surface of the $CaCl_2$ solution is great enough, in this instance, to allow the sodium alginate/cell suspension to assume the most physically favorable shape; a sphere (maximum volume for minimum surface area). Air within the tube bleeds through an opening in the stopper. This results in "cross-linking" of the gel and in the formation of a high viscosity shape-retaining protective temporary capsule containing the suspended tissue and its medium. The capsules collect in the solution as a separate phase and may be separated by aspiration.

In the next step of the process, a semipermeable membrane is deposited about the surface of the temporary capsules by "cross-linking" surface layers. This may be effected by subjecting the gelled temporary capsules to an aqueous solution of a polymer containing cationic groups reactive with anionic functionalities in the gel molecules. Polymers containing acid reactive groups such as free imine or amine groups are preferred. In this situation, the polysaccharide gum is crosslinked by interaction (salt bond formation) between the carboxyl groups and the amine or imine groups. Permeability can be controlled within limits by selecting the molecular weight of the cross-linking polymer used and by regulating the concentration of the polymer solution and the duration of exposure. A solution of polymer having a low molecular weight, in a given time period, will penetrate further into the temporary capsules than will a high molecular weight polymer. The degree of penetration of the cross-linker has been correlated with the resulting permeability. In general, the higher the molecular weight and the less penetration, the larger the pore size. Broadly, polymers within the molecular weight range of 3,000 to 100,000 daltons or greater may be used, depending on the duration of the reaction, the concentration of the polymer solution, and the degree of permeability desired. One successful set of reaction conditions, using polylysine of average molecular weight of about 35,000 daltons, involved reaction for two minutes, with stirring, of a physiological saline solution containing 0.0167 percent polylysine. This results in membranes having an upper limit of permeability of about 100,000 daltons. Optimal reaction conditions suitable for controlling permeability in a given system can readily be determined empirically in view of the foregoing guidelines. Using this method it is possible to set the upper permeability limit of the membranes at a selected level below about 200,000 daltons.

Examples of suitable cross-linking polymers include proteins and polypeptides, either natural or synthetic, having free amino or imino groups, polyethyleneamines, polyethyleneimines, and polyvinyl amines. Polylysine, in both the D and L forms, has been used with success. Proteins such as polyargenine, polycitrulline, or polyornithine are also operable. Polymers in the higher range of positive charge density, e.g., polyvinylamine, vigorously adhere to the anionic groups of the gel molecules to form stable membranes, but the membranes are rather difficult to disrupt.

Treatment with a dilute solution of gum will tie up free amino groups on the surfaces of the capsules which otherwise may impart to the capsules a tendency to clump.

At this point in the encapsulation, capsules may be collected which comprise a semipermeable membrane surrounding a gelled solution of gum, cell-type compatible culture medium, cells, and optionally an internal matrix of collagen or another anchorage substrate. Since mass transfer should be promoted within the capsules and across the membranes, it is preferred to reliquify the gel to its water-soluble form. This may be done by re-establishing the conditions under which the gum is a liquid, e.g., removing the calcium or other multifunctional cations from the interior gel. The medium in the capsule can be resolubilized simply by immersing the capsules in phosphate buffered saline, which contains alkali metal ions and hydrogen ions. Monovalent ions exchange with the calcium or other multifunctional ions within the gum when the capsules are immersed in the solution with stirring. Sodium citrate solutions may be used for the same purpose, and serve to sequester the divalent ions.

Cell cultures encapsulated as described above may be suspended in culture media designed specifically to satisfy all of the requirements of the particular cell type involved and will continue to undergo normal in vitro metabolism. If the culture requires an environment of high molecular weight components such as serum components, these may be omitted from the extracapsular medium. Typically, the components normally ingested by cells are of relatively low molecular weight and readily diffuse across the capsule membranes into the microenvironment of the cells where they permeate the cell membrane. Products of metabolism of the cells which are secreted into the intracapsular medium, if they have a molecular weight below the upper limit of permeability of the capsule membrane, likewise diffuse thereacross and collect in the extracapsular medium.

The encapsulated cells may be cultured under conditions of, e.g., temperature, pH, and ionic environment, identical to conventional cultures. Also, cell-produced products may be harvested from the extracapsular medium or from the capsules by conventional techniques. However, the culturing technique disclosed herein has the following advantages:

1. The cells of the culture are protected from shearing forces and mechanical damage and from contamination by factors having dimensions in excess of the upper permeability limit of the membranes. This means that handling and sterility requirements normally incident to culturing procedures can be somewhat relaxed, since microorganisms cannot reach the encapsulated cells, and virus infected cells need not contaminate other cells.

2. The capsules in effect immobilize the cells within an environment in which enclosed high molecular weight materials are confined, yet lower molecular weight cell nutrients and products are readily removed and introduced. This allows the nutrient broth to be intermittently or continuously collected and supplemented as desired, without disturbing the cells.

3. Substances of interest produced by the cells are more easily recovered. Secreted cells products of molecular dimensions small enough to permeate the capsule membranes collect in the extracapsular medium in admixture with nutrients. However, high molecular weight serum components and the like are not released into the extracapsular medium, thus simplifying recovery of a cell product of interest. Secreted cell products of molecular dimensions in excess of the upper permeability limit of the membranes collect within the capsules. Of course, cell products not secreted through the cell membrane may also be of interest. These may be recovered in relatively concentrated form by isolating the capsules and subsequently selectively disrupting the capsule membranes using, for example, the technique disclosed hereinafter, and if necessary by disrupting the cell membranes.

4. The intracapsular volume provides an environment well suited for cell division. Suspension cultures have been observed to undergo mitosis within the capsule. Anchorage dependent cells which in normal cultures grow in a two-dimensional monolayer multiply to form an array within the capsule. Such cells use the interior surfaces of the membrane as a substrate and/or anchor to the high molecular weight materials set forth above which are disposed within the capsule. This leads to significant increases in cell density as compared with conventional cultures. The ongoing viability of such cell clusters is aided by the fact that the surface area to volume ratios of the capsules can be quite large, and thus all cells have access to required nutrients, oxygen, etc.

In certain situations it would be advantageous to selectively disrupt the capsule membranes to release the cells without damage. One notable example is in the production of interferon (INF). Cells capable of producing INF must be subjected to certain viruses or nucleic acids in preparation for the INF production stage. Also, in several INF induction procedures, reagents are added to the culture to inhibit protein synthesis. Accordingly, the growth stage of the culturing process must be conducted under conditions quite different from the INF induction stage. If the substances used for INF induction are of a molecular weight in excess of the upper permeability limit of the capsule membranes (as will be the case in virus inductions) the induction process cannot be accomplished in the encapsulated cell culture. Accordingly, INF producing cells, if grown within the capsule, would have to be released by disruption of the membrane in order to be subjected to the induction process.

Disruption of Membranes

Cells confined in membranes of the type set forth above may be released by a process involving commercially available reagents having properties which do not significantly adversely affect the encapsulated cells. First, the capsules are separated from their suspending medium, washed thoroughly to remove any contaminants present on the exterior of the microcapsules, and then dispersed, with agitation, in a mixed solution of monatomic, multivalent cations such as calcium ions and a stripping polymer having plural anionic moieties such as a salt of a polysulfonic or polyphosphoric acid. Heparin, a natural sulfonated polysaccharide, is preferred for this step. The anionic charge density of the stripping polymer used should be equal to or preferably greater than the charge density of the polyanionic material originally employed to form the membranes. The molecular weight of the polymer should be at least comparable to and preferably greater than the molecular weight of the polymer having plural cationic groups used in forming the membrane. Within the suspension of capsules in the mixed solution, the calcium ions compete with the polycationic polymer chains used to form the membrane for anionic sites on the water-soluble gum. Simultaneously, the heparin or other polymer having plural anionic moieties dissolved in the solution competes with the gum in the membrane for cationic sites on the polymer chains. This results in a water-dispersable or preferably water-soluble complex of e.g., polylysine and heparin, and in association of the monatomic cations with molecules of the gel.

This step renders the membrane suseptible to dissolution upon subsequent exposure to a sequestering agent which completes the disruption process by taking up monatomic ions from the gel. Capsule membrane debris which remains in the medium, if any, can be easily separated from the cells.

The currently preferred solution for the first stage of the selective disruption process comprises 1.1% calcium chloride (w/v) and between 500 to 1,500 units of heparin per milliliter of solution. A volume of microcapsules is added to this solution sufficient to constitute between about 20% and 30% of the total volume of suspension. Calcium chloride and heparin are preferred for disrupting membranes of cell-containing capsules since both reagents are physiologically compatible with most cells and therefore minimize the possibility of cell damage. Mixtures of aluminum salts or other multivalent cations (but not Mg++ ions) may also be used together with the polysulfonic or polyphosphoric acid salts of the type set forth above.

In general, the concentrations of monatomic ions and anionic polymer used in this step may vary widely. Optimum concentrations may be readily determined empirically, and depend on exposure time as well as the particular polymer used to form the membranes.

The currently preferred sequestering agent for performing the selective disruption is sodium citrate, although other alkali metal citrate salts and alkali metal EDTA salts may also be used. When sodium citrate is employed, the optimum concentration is on the order of 55 mM. It is preferred to dissolve the citrate or other sequestering agent in isotonic saline so as to minimize cell damage.

The invention will be further understood from the following non-limiting examples.

Example 1: Insulin Production

Islets of Langerhans are obtained from human cadaver or from animal pancreas and added to a complete tissue culture (CMRL-1969 Connaught Laboratories, Toronto, Canada) at a concentration of approximately $10^3$ islets per 100 ml. The tissue culture contains all nutrients needed for continued viability of the islets as well as the amino acids employed by the Beta cells for making insulin. One milliliter of a $10^3$ islet per milliliter suspension is then added to a 2 milliliter volume of 1.2 percent sodium alginate (Sigma Chemical Company) in physiological saline.

Next, a 1.2 to 1.5 percent calcium chloride solution is used to gel droplets of the solution formed as set forth above. Droplets on the order of 500–1000 microns in diameter emanating from the tip of the needle immediately gel upon entering the calcium solution. The gelled capsules are then transferred to a beaker containing 15 ml of a solution comprising one part of a 2% 2 (cyclohexylamino) ethane sulfonic acid buffer solution in 0.6% NaCl (isotonic, ph=8.2) diluted with 20 parts 1.1% CaCl2. After a 3 minute immersion, the capsules are washed twice in 1.1% CaCl2.

The capsules are then transferred to a 32 ml solution comprising 1/30 of one percent polylysine (average MW 35,000 daltons) in physiological saline. After 3 minutes, the polylysine solution is decanted. The capsules are washed with 1.1% $CaCl_2$, and optionally resuspended for 3 minutes in a solution of polyethyleneimine (MW 40,000–60,000) produced by diluting a stock 3.3% polyethyleneimine solution in morpholino propane sulfonic acid buffer (0.2 M, ph=6) with sufficient 1.1% CaCl2 to result in a final polymer concentration of 0.12%. The resulting capsules, having "permanent" semipermeable membranes, are then washed twice with 1.1% $CaCl_2$, twice with physiological saline, and mixed with 10 ml of 0.06 percent alginic acid solution.

The capsules resist clumping, and many can be seen to contain islets of Langerhans. Gel on the interior of the capsules is reliquified by immersing the capsules in a mixture of saline and citrate buffer (ph-7.4) for 5–10 minutes. Lastly, the capsules are suspended in CMLR 1969 medium.

Under the microscope, these capsules are seen to consist of a very thin membrane which encircles an islet within which individual cells can be seen. Molecules having a molecular weight up to about one-hundred thousand can traverse the membranes. This allows oxygen, amino acids, nutrients, and plasma components used in culture media (i.e., lower molecular weight fetal calf plasma components) to reach the islet and allows insulin to be secreted.

After repeated washings in physiological saline, microcapsules made in accordance with the above procedure are suspended in CMRL-1969. When eight days old, in the presence of 600 mg/dl glucose, the capsules secreted into the extracapsular medium, in one run, 80 microunits/ml/minute of insulin per 15 islets. In a second run, 85 microunits/ml/minute of insulin per 15 islets were produced in the same amount of time. One week old capsules, in the same medium, but in the presence of 100 mg/dl glucose, in a first run, secreted about 1/10 as much insulin in two subsequent runs.

Example 2: INF-$\beta$ Production

Human fibroblasts obtained by treating human foreskin tissue with trypsin and EDTA for 5 minutes at 37° C. in a known manner are suspended in a complete growth medium (CMLR 1969, Connaught Laboratories) supplemented with 40% (v/v) purified fetal calf serum, and 200 $\mu$g/ml purified calf skin collagen. The density of the cell suspension is about $1.5 \times 10^7$ cells/ml. Temporary alginate capsules containing the fibroblasts are formed as set forth in Example 1. Semipermeable membranes are deposited in surface layers of the capsules by suspending them in a 0.005% (w/v) aqueous solution of polylysine, (MW 43,000 daltons) for 3 minutes.

The resulting capsules are suspended in CMLR-1969 supplemented with 10% fetal calf serum. The foregoing steps are all conducted at 37° C. After incubation at the same temperature, the capsules, if examined under the microscope, will be found to contain fibroblasts which have undergone mitosis and display three-dimensional fibroblastic morphology within the microcapsules.

After 4–5 days of incubation, the encapsulated fibroblasts are subjected to an INF-$\beta$ superinduction technique according to the Vilcek procedure. Under a 5% $CO_2$ atmosphere (95% air), the capsule suspension is incubated at 37° C. for one hour in the presence of 100 $\mu$g/ml Poly I-Poly C, a double stranded RNA (known INF-$\beta$ inducer) available from PL Biochemicals, Milwaukee, Wis. and 50 $\mu$g/ml cycloheximide (protein synthesis inhibitor, Calbiochem, La Jolla, Calif.) After one hour, the suspended capsules are washed in medium (CMLR-1969) containing 50 $\mu$g/ml cycloheximide and then resuspended in the same solution for 3 hours at 37° C. under a 5% $CO_2$ atmosphere. At the completion of this incubation the washing step is repeated and the capsules are resuspended in medium containing 50 $\mu$g/ml cycloheximide and 5 $\mu$g/ml actimomycin D (a known RNA synthesis inhibitor, Calbiochem) and incubated for 2 hours at 37° C. under a 5% $CO_2$ atmosphere. The capsules are then washed twice in medium and suspended in serum-free medium at 37° C. for 18–24 hours, during which time the fibroblasts secrete INF-$\beta$, which has a molecular weight on the order of 21,000 daltons and may be harvested from the extracapsular medium.

Example 3: INF-$\beta$ Production

The procedure of Example 2 is repeated, except that prior to induction the capsule membranes are selectively disrupted so that the Poly I.Poly C can more easily gain access to the fibroblasts. The disruption procedure is conducted as follows.

10 ml portions of microcapsule suspensions containing about 500–1000 capsules per ml are allowed to settle and the suspension medium is aspirated off. The capsules are washed twice with phosphate buffered saline (PBS, pH=7.4). The washed capsules are then mixed with a 3.0 ml aliquot of PBS containing 1000 units/ml heparin and 1.1% (w/v) $CaCl_2$. The suspension is agitated at 37° C. for 3 minutes, after which the capsules are allowed to settle, the supernatant is aspirated off, and the capsules are washed twice with 3.0 ml of 0.15 M NaCl. After aspiration of the second wash solution, the capsules are mixed with 2.0 ml of a mixed solution comprising equal volumes of 110 mM sodium citrate and 0.15 M NaCl (pH=7.4). The mixture is hand vortexed for 1 minute to induce dissolution of the membranes after which cells are washed twice in medium.

The cells are then suspended in medium, subjected to the induction procedure set forth in example 2, and then reencapsulated as set forth in Example 2. The capsule suspension is then incubated in serum-free medium for 18–24 hours, during which time INF-$\beta$ is secreted from the cells, permeates the capsule membranes, and collects in the extracapsular medium.

Examples 2 and 3, if conducted with Poly I-Poly C (5S) (sedimentation value, Poly I and Poly C annealed to form double stranded RNA) result in the following INF-$\beta$ production levels, in units of INF-$\beta/10^5$ cells:

|  | 1. | 2. |
|---|---|---|
| Example 2 | 25 | 25 |
| Example 3 | 2,500 | 2,500 |

Examples 2 and 3, if conducted with Poly I-Poly C (12S) (sedimentation value, double stranded as purchased) result in the following INF-$\beta$ production levels, in units of INF-$\beta/10^5$ cells:

|  | 1. | 2. |
|---|---|---|
| Example 2 | 25 | 25 |
| Example 3 | 2,500 | 2,500 |

The one-hundred fold increase in production using the procedure of Example 3 over that of Example 2 is believed to be due, at least in part, to the fact that the Poly I.Poly C has better access to the cells in the Example 3 procedure.

Example 4

The procedure of Example 2 is repeated except that capsules containing no collagen are employed. The encapsulated cells were grown in conventional monolayer culture, treated with trypin, and induced with Poly I.Poly C (5S) and microencapsulated simultaneously. The extracapsular medium is found to contain 2,500 units INF-$\beta/10^5$ cells.

Example 5: Monoclonal Antibodies

Hybridoma cells obtained from Herman Eisen at MIT were culture to a density of $3.0 \times 10^6$ cells/ml. These cells had been fused from mouse spleen cells and mouse myeloma cells in a manner now well known in the prior art and constituted an immortal cell line which in culture produced antibodies against dinitrophenyl bovine serum albumin. Three ml aliquots of the cell suspension were made up by adding 2.1 ml of suspension containing 1.4% sodium alginate to 0.6 ml fetal calf serum and 0.3 ml physiological (150 mM) saline. Droplets of the suspension were immediately gelled in CaCl$_2$ solution and then treated with a 0.016 weight percent solution of poly L lysine. The interior of the resulting capsules was then reliquified by immersion in a solution of one part 110 mM sodium citrate and three parts 150 mM saline for 6 minutes. The capsules containing hybridoma cells were then suspended in a mixture of RPMI-1640 medium (Gibco) containing 20% heat inactivated fetal calf serum.

Figure 2:
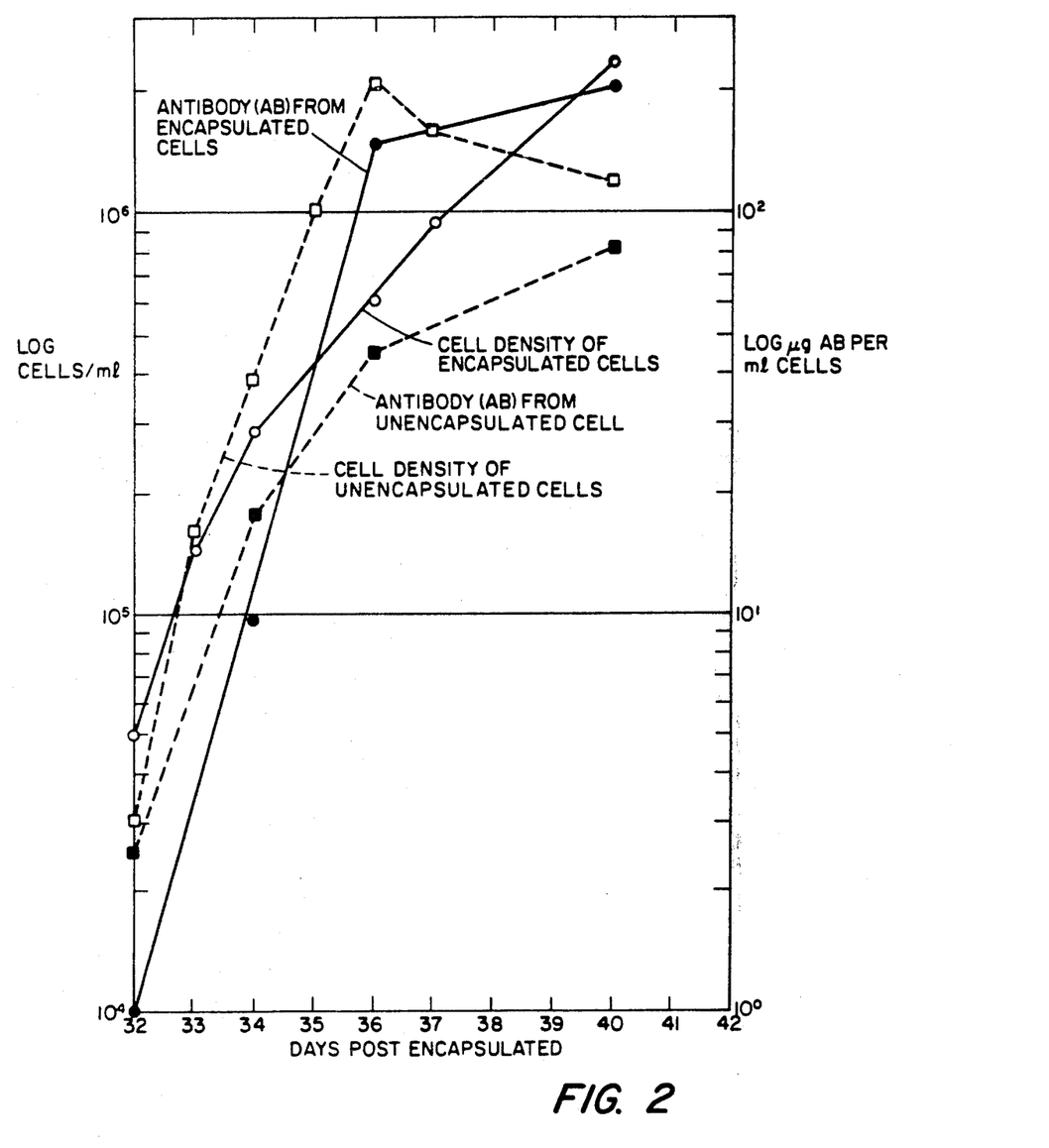

Cell counts of encapsulated and unencapsulated hybridoma cultures, and the amount of monoclonal antibody produced by both the encapsulated and unencapsulated cultures were determined periodically. The results are set forth in graphical form in FIG. 2.

Example 6: INF-α from Leukocytes 30 ml buffy coats obtained from the American Red Cross were treated with 3.0 ml of 5% EDTA and repeated 10 minute exposures to 0.83% NH$_4$Cl at 4° C. to lyse the red cells. A five minute centrifuge (1200 rpm at 4° C.) between NH$_4$Cl treatments separated debris from the remaining intact leukocytes. The cells were next suspended in MEM (minimum essential medium, serum free-Gibco), diluted by a factor of 100, and stained with tryptan blue for 15 minutes. A cell count conducted on a sample showed that about $1.3 \times 10^9$ leukocytes per 30 ml buffy coat survived. The cells were then suspended at a density of $1 \times 10^7$ cells/ml in medium supplemented with 2% heat inactivated fetal calf serum.

Induction was effected by exposing the cell suspension to Sendai virus (various concentrations in heamagglutinating units/ml-Flow Laboratories, Md.) for one hour at 37° C. with stirring. The virus was then separated from the cell by centrifugation at room temperature and the cells were resuspended in equal volumes of MEM-4% heat inactivated fetal calf serum and 1.4% sodium alginate. Capsules were formed as set forth above and then resuspended in serum-free and serum-containing media. There were no significant differences in the quantities of INF detected in the extracapsular medium of these test samples. INF production levels were also identical in unencapsulated control cultures. The results of these experiments are set forth below

| Units Sendai Virus (HA Units/ml) | INF Produced Units 10$^7$ Cells |
|---|---|
| 600 | 10 |
| 300 | 20 |
| 150 | 33 |
| 75 | 50 |

Example 7: INF-α from Lymphoblastoids

Namalwa cells from the American Type Culture Collection were grown both in conventional culture and within microcapsules in RPMI-1640 medium supplemented with 10% heat inactivated fetal calf serum. Volumes of the cell suspensions were then subjected to INF induction and production procedures, with one volume encapsulated and the other unencapsulated. The cultures contained substantially equal numbers of cells. To both the encapsulated and unencapsulated cultures was added 25 mg/ml bromo deoxyuridine in double distilled water to inhibit mitosis. After incubation for 36 hours at 37° C., the cells of both cultures were washed and then suspended in RPMI1640 medium supplemented with 2% heat inactivated fetal calf serum.

The encapsulated culture was then treated to selectively disrupt the capsule membranes. The capsules were washed three times in phsiological saline incubated in 1000 units/ml heparin solution containing 1.1% CaCl$_2$ for 10 minutes at 37° C., and then rewashed in saline. The washed capsules are next incubated for 5 minutes at 37° C. with dilute sodium citrate solution in physiological saline. Agitation of the capsule suspension at this point results in dissolution of the membranes and release of the Namalwa cells. The cell suspension is then centrifuged to remove debris and washed several times in citrate/saline solution.

Both cultures were next suspended in fresh RPMI-1640 culture medium supplemented with 2% heat inactivated fetal calf serum and buffer (pH=7.4) at a density of $1.0 \times 10^6$ cells/ml.

To both the conventional culture and the formerly encapsulated culture were then added the Bankowski strain of Newcastle Disease Virus in amniotic fluid. The virus was at a concentration of $1.0 \times 10^8$ pfu/ml and was purchased from Poultry Health Laboratories, Davis, Calif. One ml of the virus was added for each 10 ml of cell suspension. The cultures were incubated for 24 hours at 37° C.

The conventional culture was then divided into five parts (1–5 below); the formerly encapsulated culture was divided into 4 parts (6–9 below). Each of the 9 aliquots of culture were then assayed for INF production following the treatments set forth below.

1. untreated
2. resuspended in RPMI-1640 medium with 2% heat inactivated fetal calf serum
3. resuspended in RPMI-1640 medium serum-free
4. encapsulated together with RPMI-1640 medium and 5% heat-inactivated fetal calf serum-capsules suspended in serum-free medium
5. encapsulated together with RPMI-1640 medium and 5% heat-inactivated fetal calf serum-capsules suspended in medium with 2% fetal calf serum
6. resuspended in serum-free medium
7. resuspended in medium containing 2% heat-inactivated fetal calf serum
8. reencapsulated together with medium plus 5% heat-inactivated fetal calf serum-capsules suspended in serum-free medium
9. reencapsulated together with medium plus 5% heat-inactivated fetal calf serum-capsules suspended in medium plus 2% serum The following table sets forth the quantity of cells required in each of the cell cultures 1–9 to produce 1 unit of INF α:

| 1 | 30 | 6 | 40 |
|---|---|---|---|
| 2 | 45 | 7 | 40 |
| 3 | — | 8 | 1000, 360 |
| 4 | 680 | 9 | 200, 100 |
| 5 | 2000 | | |

Other embodiments are within the following claims.
What is claimed is:
1. A process for producing a substance which is produced by living cells, said process comprising the steps of:
A. encapsulating said cells within semipermeable membranes having a selected upper limit of permeability, said encapsulating being effected by forming said semipermeable membranes by reacting cationic groups on polymer chains having a molecular weight greater than about 3000 with anionic groups on a polysaccharide gel encapsulating said cells to cross-link surface layers of said polysaccharide gel to form said semipermeable membranes;

B. suspending said encapsulated cells in an aqueous culture medium;

C. allowing said cells to undergo metabolism in vitro and to produce said substance; and D. harvesting said substance either from said aqueous medium or from within said membranes.

2. The process of claim 1 wherein said cells comprise hybridoma cells.

3. The process of claim 1 wherein said encapsulation step (A) is effected by the steps of:
(1) suspending the cells in an aqueous medium physiologically compatible therewith and containing a water-soluble gum having plural anionic moieties;
(2) forming the suspension into droplets containing the cells;
(3) subjecting the droplets to a solution of multivalent, physiologically compatible cations to gel the droplets to form discrete, shape-retaining, water-insoluble temporary capsules as said polysaccharide gel encapsulating said cells; and
(4) cross-linking surface layers of said temporary capsules to produce semipermeable membranes about said gelled droplets by subjecting them to said polymer containing cationic groups reactive with said anionic groups.

4. The process of claim 3 comprising the additional step of resolubilizing the gel within the membrane produced in step (4).

5. The process of claim 1 wherein said substance has a molecular weight below said selected upper permeability limit, said process comprising the step of allowing the substance to diffuse through said membranes into said aqueous medium and harvesting said substance therefrom.

6. The process of claim 1 or 5 wherein said cells are encapsulated together with a complete cell culture medium sufficient to maintain said cells and to allow biosynthesis of said substance in vitro.

7. The process of claim 1 or 5 wherein the aqueous medium used in step (B) is a complete cell culture medium sufficient to maintain said cells and to allow biosynthesis of said substance in vitro.

8. The process of claim 6 wherein a component having a molecular weight in excess of the upper permeability limit of said membranes is needed by said cells in order to allow in vitro biosynthesis of said substance, said process comprising the additional step of encapsulating said component together with said cells.

9. The process of claim 1 or 5 wherein said cells are mammalian cells.

10. The process of claim 1 or 5 comprising the additional step of allowing said cells to undergo mitosis within said capsule.

11. The process of claim 1 or 5 wherein said cells are cells which have been genetically modified.

12. The process of claim 1 or 5 wherein during said encapsulation step (A), spheroidal microcapsules having a diameter from about 0.4 to 1.0 mm are produced.

13. The process of claim 1 or 5 wherein the substance harvested in step (E) is selected from the group consisting of insulin, glucagon, prolactin, somatostatin, thyroxin, steroid hormones, pituitary hormones, interferons, FSH, and PTH.

14. The process of claim 1 or 5 wherein the substance harvested in step (E) is selected from the group consisting of hormones, interferons, lymphokines, and antibodies.

15. The process of claim 1 or 5 wherein the cells encapsulated in step (A) require contact with a component having a molecular weight in excess of the upper permeability limit of said membranes in order to maintain production of said substance, said component being encapsulated together with said cells in step (A) and the aqueous culture medium used in step (B) being substantially free of said component.

16. The process of claim 1 wherein said selected upper limit of permeability is below about $1.5 \times 10^5$ daltons.

17. The process of claim 1 wherein said cells comprise hybridoma cells, said substance comprises monoclonal antibodies having a molecular weight in excess of said selected upper limit of permeability, and said antibodies are harvested from within said membranes.

18. A system for producing a substance which is produced by living cells comprising viable cells encapsulated within semipermeable membranes and suspended in an aqueous culture medium for said cells, the semipermeable membranes of said encapsulated viable cells having an upper limit of permeability sufficient to allow traverse of nutrients required by said cells, said semipermeable membranes comprising a polysaccharide gel having plural anionic groups cross-linked with a polymer having a molecular weight greater than about 3000 and having plural cationic groups, said semipermeable membranes encapsulating suspended viable, healthy, physiologically active cells disposed in a medium which includes all components (A) needed to maintain viability of said cells and which components are of a size in excess of the upper permeability limit of said membranes, said aqueous culture medium comprising all components (B) needed to maintain viability of said cells having a molecular weight below the upper permeability limit of said membranes.

19. The system of claim 18 wherein said components (A) comprise serum components.

20. The system of claim 18 wherein said cells comprise mammalian cells.

21. The system of claim 18 wherein said cells comprise microorganisms.

22. The system of claim 18 wherein said cells comprise genetically modified cells.

23. The system of claim 18 wherein said cells comprise hybridoma cells.

24. The system of claim 18 wherein said cells comprise cells capable of producing in vitro a substance selected from the group consisting of hormones, interferons, lymphokines, and antibodies.

25. The system of claim 18 wherein said cells comprise cells capable of producing in vitro a substance selected from the group consisting of insulin, glycogen, growth hormones, pituitary hormones, steroid hormones, prolactin, somatostatin, PTH, and FSH.

* * * * *